United States Patent [19]

Henry

[11] Patent Number: 5,516,768

[45] Date of Patent: May 14, 1996

[54] UNCOMPETITIVE INHIBITION OF STEROID AND 5α-REDUCTOSE

[75] Inventor: Michael Henry, Radnor, Pa.

[73] Assignee: SmithKline Beecham Corporation, Philadelphia, Pa.

[21] Appl. No.: 13,509

[22] Filed: Feb. 4, 1993

Related U.S. Application Data

[63] Continuation-in-part of Ser. No. 927,263, Sep. 16, 1992, abandoned.

[30] Foreign Application Priority Data

Mar. 16, 1990 [GB] United Kingdom ................... 9006023

[51] Int. Cl.⁶ ..................................................... A01N 45/00
[52] U.S. Cl. .......................................... 514/170; 552/500
[58] Field of Search ............................... 514/170; 552/500

[56] References Cited

U.S. PATENT DOCUMENTS

| | | | |
|---|---|---|---|
| 5,026,882 | 6/1991 | Holt et al. | 552/506 |
| 5,032,586 | 7/1991 | Metcalf | 514/177 |
| 5,041,433 | 8/1991 | Holt et al. | 514/176 |

Primary Examiner—Paul J. Killos
Attorney, Agent, or Firm—Wayne J. Dustman; Stephen Venetianer; Edward T. Lentz

[57] ABSTRACT

Invented are compositions of competitive and uncompetitive inhibitors of steroid 5-α-reductase, pharmaceutical compositions containing the compositions of inhibitors and methods of using these compositions to inhibit steroid 5-α-reductase. Also invented in the method of co-administating a 5-α-reductase inhibitor and further active ingredients.

12 Claims, 3 Drawing Sheets

UNCOMPETITIVE INHIBITION OF STEROID AND 5α-REDUCTOSE

This application is a continuation-in-part of Ser. No. 07/927,203 filed Sep. 16, 1992 now abandoned.

COMPOSITIONS

This invention comprises a composition containing one of certain selected compounds which are competitive inhibitors of steroid 5-α-reductase, combined with one of certain selected compounds which are uncompetitive inhibitors of steroid 5-α-reductase. The composition which contains this new combination of medicinal agents demonstrates improved suppression of plasma dihydrotestosterone (DHT) and improved prostate and seminal vesicle weight reduction.

Steroid 5-α-reductase is a NADPH-dependent enzyme that mechanistically converts testosterone (T) to DHT. The individual compounds of the chimed compositions produce 5-α-reductase inhibiting activity by binding to a specific enzyme species at a specific stage of the reductive process. Combining inhibitors that bind to a different enzyme species at different stages of the reductive process has been found to lower the level of plasma DHT and to reduce the weight of the prostate and seminal vesicles to an extent beyond which a single inhibitor can achieve alone.

This invention also comprises the co-administration of a 5-α-reductase inhibiting compound, competitive or uncompetitive, and further active ingredients.

BACKGROUND OF THE INVENTION

Steroid 5-α-reductase is a NADPH-dependent enzyme that converts testosterone to DHT. Recognition of the importance of elevated DHT levels in various disease states has stimulated many efforts to synthesize inhibitors of this enzyme.

The first inhibitor described was 4-androsten-3-one-17β-carboxylic acid by Hsia and Voight in 1973. *J. Invest. Dermat,* 62:224–227. (4R)-5,10-seco-19-norpregna-4,5-diene -3,10,20-triane was the next inhibitor to be described and also has found utility as an affinity label for 5-α-reductase. Robaire, B., et al., (1977), *J. Steroid Biochem.* 8:307–310. (5α,20-R)-4-diazo-21-hydroxy-20-methylpregnan-3-one has been reported as a potent, time-dependent inhibitor of steroid 5-α-reductase. Blohm, T. R., et al., (1980), *Biochem. Biophys. Res. Comm,* 95:273–280; U.S. Pat. No. 4,317,817, Mar. 2, 1982. 17β-N,N-diethylcarbamoyl-4-methyl-4-aza -5-α-androstan-3-one is exemplary of a group of 4-aza steroid inhibitors of steroid 5-α-reductase described in U.S. Pat. No. 4,377,584 which issued Mar. 22, 1983, and in Liang, T., et al., (1983), *J. Steroid Biochem,* 19:385–390. 17α-acetoxy-6-methylene-pregn-4-ene-3,20-dione also has been shown to be a time-dependent inactivator of steroid 5-α-reductase. Petrow, V., et al., (1981), *Steroids* 38:121–140.

Other steroid 5-α-reductase inhibitors also have been described. U.S. Pat. No. 4,361,578 which issued Jun. 2. 1986, describes a class of homosteroid enzyme inhibitors. U.S. Pat. No. 4,191,759 discloses amides of 17β-carboxy-4-androsten-3-one that are active as steroid 5-α-reductase inhibitors. Japanese Patents J60146855-A and J60116657-A disclose various aniline derivatives having numerous activities including 5-α-reductase inhibiting activity. Japanese Patent I60142941-A discloses phenyl-substituted ketones having 5-α-reductase inhibiting activity and European Patent EP173516-A discloses various phenyl-substituted amides having similar activity. Shiseido referenced terpene derivatives that are active inhibitors of steroid 5-α-reductase. Japanese Patent J59053417-A.

Recently it has been shown that steroid 5-α-reductase follows an ordered kinetic mechanism (Houston et al., (1987), *Steroids* 49: 355–369; Metcalf, B., et al., (1989) *Bioorganic Chemistry* 17:372–276) in which the nicotinamide confactors are the first substrate binding to the enzyme and the last product released from the enzyme (FIG. 1 ). Dead-end inhibitors of bisubstrate enzymes which follow ordered kinetic mechanisms can associate to one or more existing enzyme species. With steroid 5-α-reductase, enzyme forms to which such a steroidal-inhibitor might bind would include free enzyme, E, and enzyme binary complexes with cofactor, E-NADPH and E-NADP$^+$. For example, that 4-aza steroidal inhibitors, such as N-t-butyl -5-α-androst- 1-ene-4-aza-17β-carboxamide-3-one (compound A) (Liang, et al., (1985), *Endocrinology* 117:571–579), inhibit enzyme activity by forming an enzyme-NADPH-inhibitor dead-end complex (E-NADPH-1, FIG. 1).

In this context, the binding of inhibitors to each of these enzyme forms would be kinetically distinct as described in Irwin H. Segal, *Enzyme Kinetics,* Pub: John Wiley & Sons, Inc. (1975). The response of the velocity of enzyme catalysis with varying concentrations of testosterone in the presence of an inhibitor that binds to the E-NADPH complex can be described by equation 1; this model is denoted as competitive inhibition versus the variable substrate, in this case testosterone. Similarly, the model for an inhibitor that preferentially associates to the E-NADP$^+$ complex would be described by equation 2; such a compound is referred to as an uncompetitive inhibitor versus the variable substrate. In equations 1 and 2, v is the observed velocity of product formation, $V_m$ is the maximal enzyme velocity at saturating concentrations of the variable substrate (A), I is the concentration of the inhibitor with apparent inhibition constants of $K_{is}$ or $K_{ii}$, and $K_a$ is the apparent Michaelis constant for the variable substrate.

$$v = V_M A / [K_a(1+I/K_{is})+A] \tag{1}$$

$$v = V_M A / [K_a + A(1+I/K_{ii})] \tag{2}$$

Velocities (v) determined at variable concentrations of substrate (A) and inhibitor (I) are evaluated by non-linear curve fittings with computer programs as described by Cleland (Cleland, W. W. (1979) *Methods in Enzymology* 63, 103–138), to determine the best fit to equations 1 or 2. The results of these analyses are typically expressed in double reciprocal plots: 1/velocity versus 1/[testosterone]. The patterns in FIG. 1 are characteristic of a competitive and a uncompetitive inhibitor versus the second substrate in an ordered kinetic mechanism, and can be used to distinguish between the binding of a reversible dead-end inhibitor to E-NADPH or E-NADP$^+$, respectively. Since the same uncompetitive model (equation 2) is used to describe an inhibitor that binds to either E-NADPH or E-NADP$^+$ upon variation of the first substrate which binds to the surface of an ordered-enzyme, discrimination between these two mechanisms would not be possible by such an experiment with varying NADPH; the results from such an experiment can be used, however, to discriminate from a mechanism of inhibition resulting from binding to free enzyme (E).

The effects of inhibitors which act by these two differing mechanisms under comparable conditions are shown in FIG. 2; in this example, the concentration of each inhibitor has been set to be equal to its inhibition constant ($K_{ii}$ or $K_{is}$) and the Michaelis-constant for substrate ($K_m$) has been set a 1 concentration unit. Curves B and C represent inhibitors that preferentially bind to the E-NADPH and E-NADP$^+$ complexes while curve A represents the uninhibited velocity. Note that curves A and B intersect on the ordinate (competitive pattern) while curves A and C are parallel (uncompetitive pattern). From this plot, it can be seen that a competitive inhibitor (E-NADPH-I) is more efficient at low substrate concentration, while the uncompetitive inhibitor (E-NADP$^+$-J) is more efficient at higher concentrations of substrate. The intersection point for these two curves occurs at the concentration of substrate that equal its $K_m$.

A single molecule that could bind equally well to both E-NADPH and E-NADP$^+$ would demonstrate the additive effects in slope and intercept of the two double-reciprocal plots. This is described by equation 3, and is represented by carve D in FIG. 2.

$$v=V_m A/[K_a(1+I/K_{is})+A(1+I/K_{ii})] \qquad (3)$$

Inhibition by a molecule that demonstrates such a mixed (noncompetitive) mode of action is more efficient that either of the single mechanisms alone over the entire substrate concentration range. This description of a mixed mode interaction is equally applicable to inhibition of steroid 5-α-reductase in the presence of two different molecular species which interact independently with the different enzyme forms, E-NADPH and E-NADP$^+$. Thus, curve D also describes the inhibition by two compounds, each at concentrations equivalent to their inhibition constants for the E-NADPH and E-NADP$^+$ complexes. Again, the result is superior to that of the single inhibitor throughout the entire concentration range of substrate.

Such additive inhibitory effects of a competitive inhibitor (N-t-butyl-5-α-androst -1-ene-4-aza-17β-carboxamide-3-one, compound A) and an uncompetitive inhibitor (N,N-diisopropyl-androst-3,5-diene-17β-carboxamide-3-carboxylic acid, compound B) have been demonstrated in vitro with double inhibition experiments; increasing concentrations of one inhibitor in the presence of the second induces greater enzyme inhibition (FIG. 3), while also demonstrating mutually exclusive binding. For a given concentration of one of the inhibitors, which binds to ENADPH (competitive) or E-NADP$^+$ (uncompetitive), supplementation with any amount of the second would increase the observed enzyme inhibition over that of the reference inhibitor alone.

In comparison, FIG. 4 represents a model incorporating conservation of drug substance. Here, the calculated curves are based on the total chug substance relative to its respective inhibition constant: total inhibitor=constant=Σ ([inhibitor]/$K_{i,app}$). Curve A represents the uninhibited velocity, curves B and C represent the presence of only competitive or uncompetitive inhibitors, respectively, while curve D presents conservation of inhibitor substance composed of half competitive and uncompetitive inhibitors. Here, combination of inhibitors which function by the two different mechanisms is superior to the competitive inhibitors if the substrate concentration exceeds its $K_m$, and is more efficient than the uncompetitive inhibitors at low substrate concentration below $K_m$. A similar analysis versus the other substrate, NADPH, would demonstrate no difference in inhibition efficiency since both kinetic models are described by equation 2.

No prior art of combining 5-α-reductase inhibitors of different mechanistic types into a pharmaceutical composition to achieve superior results is known to the applicants.

DESCRIPTION OF THE INVENTION

Figure 1:
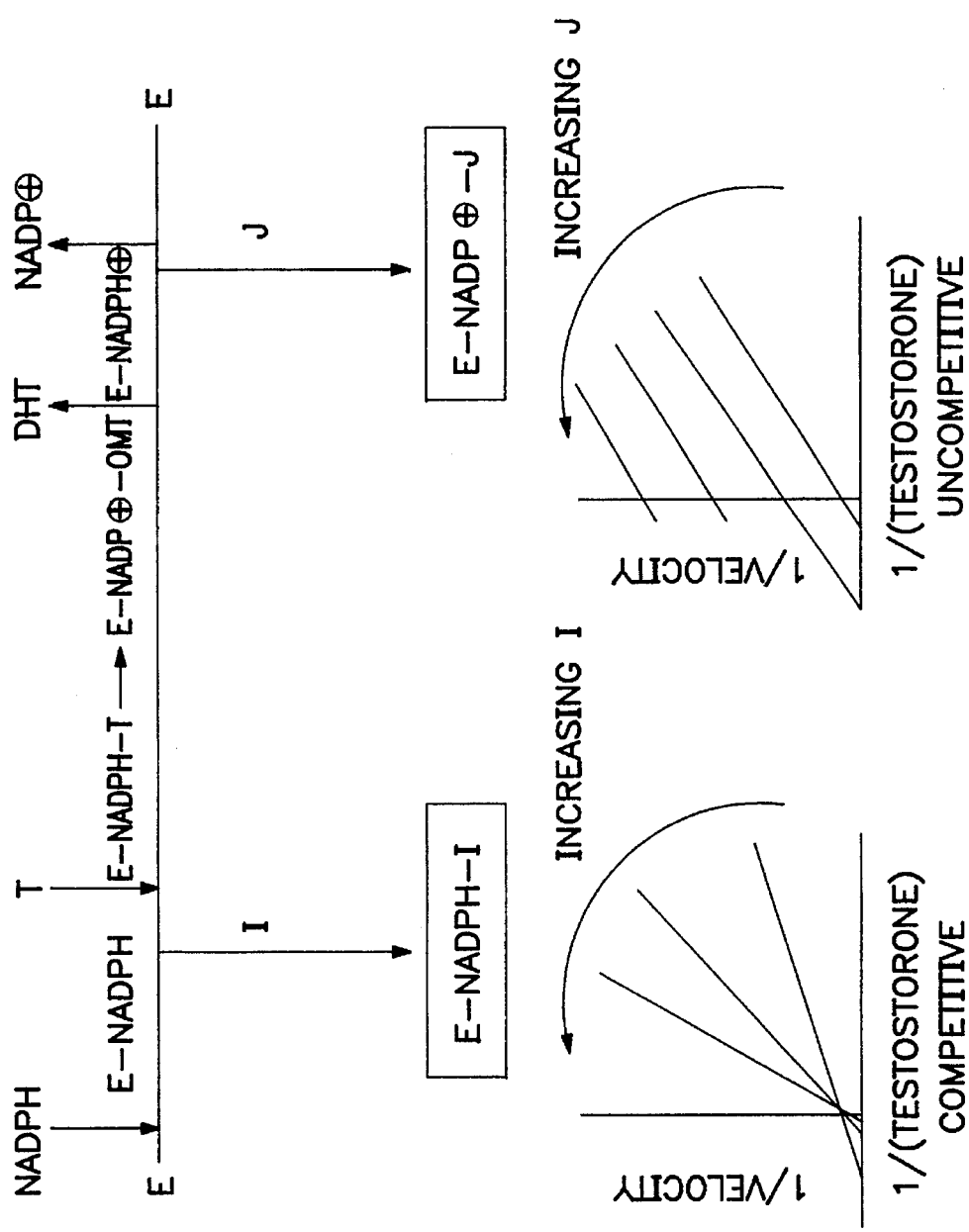
FIG. 1: Kinetic Mechanisms of Inhibition of Stexoid 5-α-Reductase by competitive and uncompetitive inhibitors. As depicted a competitive inhibitor is designated as I and an uncompetitive inhibitor is designated as J.
Figure 2:
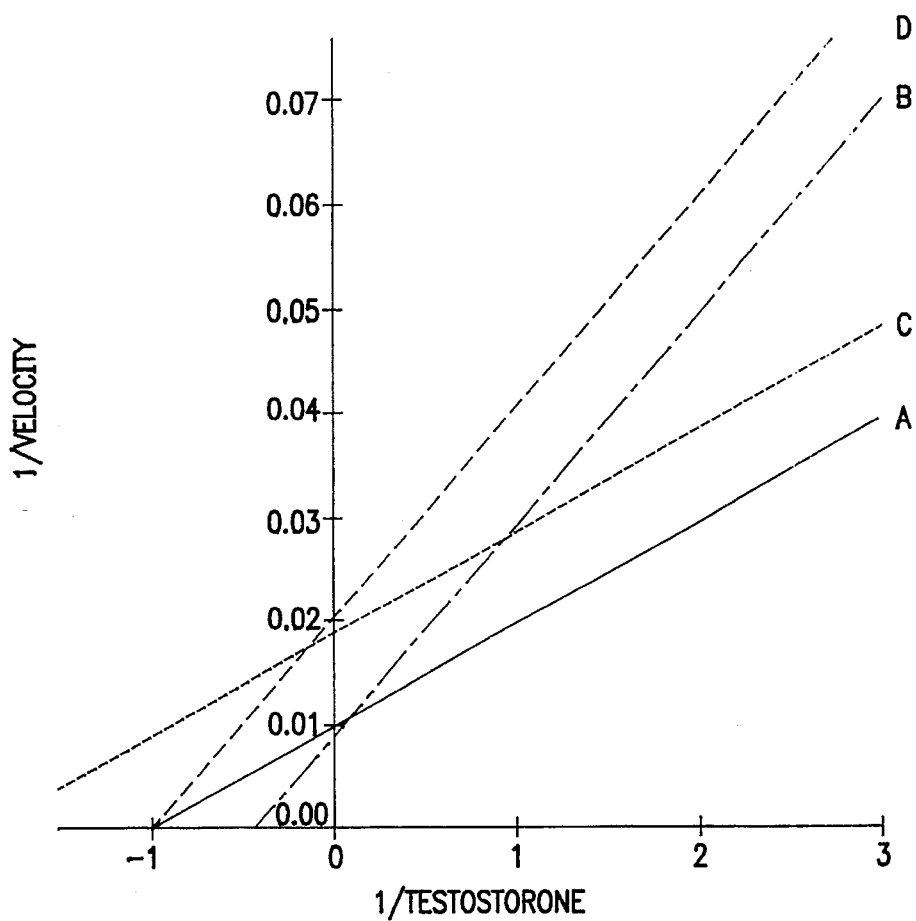
FIG. 2: Model for Inhibition of Steroid 5-α-reductance with Compounds that Bind to E-NADPH and E-NADP$^+$; Additive Effects and Inhibitors that Bind to Different Enzyme Forms.
Figure 3:
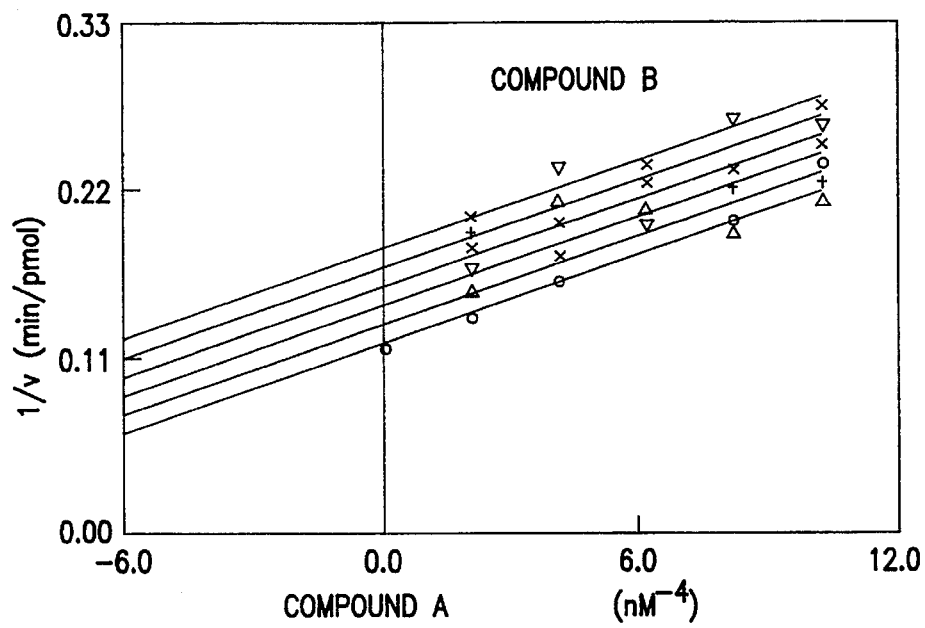
FIG. 3. Inhibition of Rat Liver Steroid 5-(α-reductase: Effects of compound A Plus compound B. Rat liver steroid 5-α-reductase was assayed at constant concentrations of T(1.0 μM) and NADPH (100 μM) in the presence of a cofactor regenerating system. The concentrations of compound A were varied from 0 to 10 mM in the presence of a 0(o), 3(Δ), 5(+),9(x), 12)◊), and 15(◊)mN were $v_i v/[1+I/K_i + J/K_j + IJ/BK_i K_i$.
Figure 4:
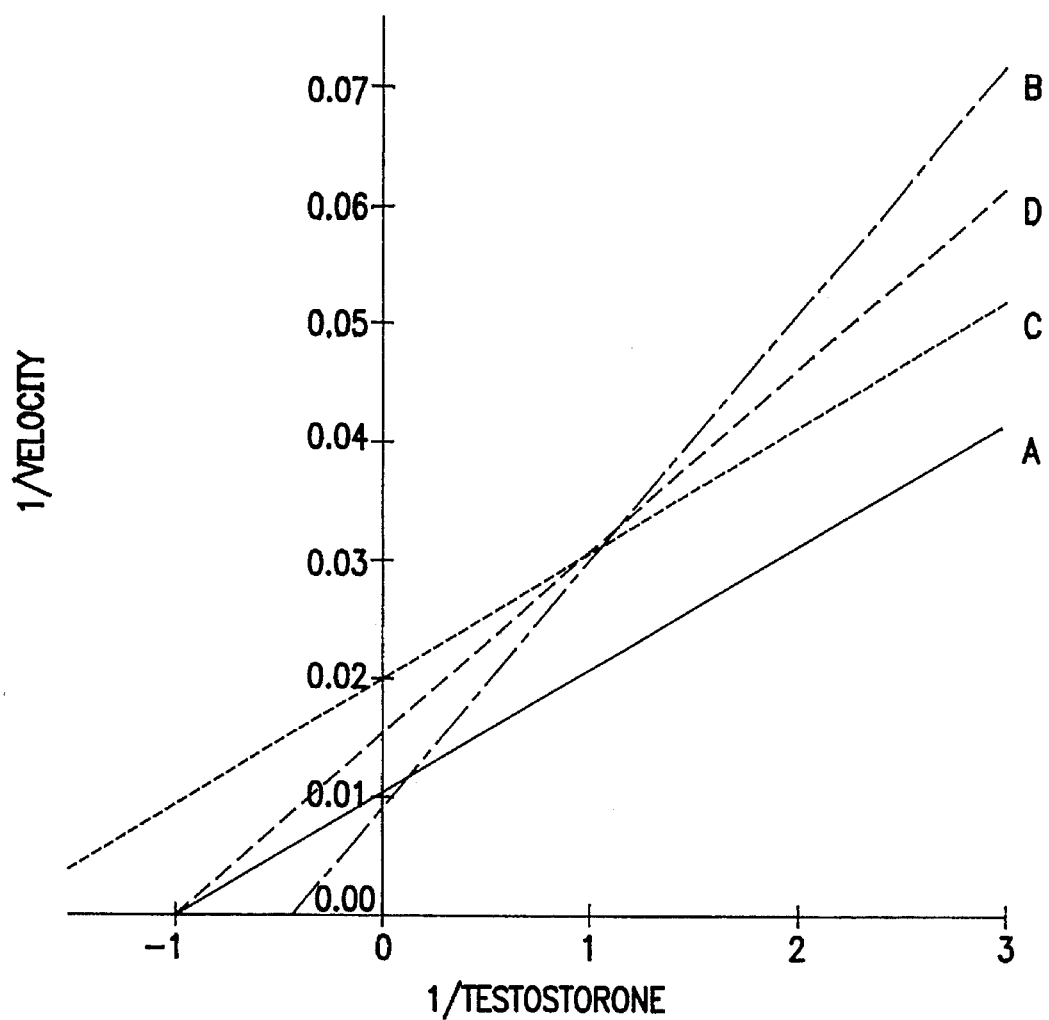
FIG. 4. Model for Inhibition of Steroid 5-α-Reductase with Compounds that Bind to B-NADPH and B-NADP$^+$: Conservation of Inhibitor Substance.

A combination selected from "competitive" and "uncompetitive" inhibitors of 5-α-reductase are used in a pharmaceutical composition to affect the enzymatic reduction of testosterone to DHT. The "competitive" inhibiting components of this invention are compounds which form an enzyme-NADPH-inhibitor dead-end complex and the "uncompetitive" inhibiting components of this invention are compounds which form an enzyme-NADP+-inhibitor dead-end complex as described above.

Also included are derivatives of these compounds which may either give rise to the parent compounds in vivo or be useful themselves, such as pharmaceutically acceptable addition salts. Salts of these compounds containing a basic group are formed with organic or inorganic acids in the presence of a basic compound by methods known to the art. For example, the compound is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such a triethylamine, butylamine, piperazine, and (trihydroxymethyl)methylamine. Prodrug derivatives include O-esters, especially the tri-O-lower alkanoyl ester having from 2–8 carbon atoms in each alkanoyl group; O-methyl ethers or sulfate esters. Separated R and S stereoisomers are also useful.

Compounds that are considered to be competitive steroid 5-α-reductase inhibitors as described above include: 3-oxo-4-aza-steroidal compounds such as N-t-butyl-5-α-androst-1-ene-4-aza-17β-carboxamide-3-one, (20R)-hydroxymethyl-4-methyl-4-aza-5-alpha-pregnane-3-one, 17β-N,N-diisopropylcarboxamide-5-α-8(14)-androsten-4-methyl-4-aza-3-one, and 17β-N-t-butylcarboxamide-5-α-8(14)-androsten-4-methyl-4-aza-3-one.

Also 3-nitro steroidal compounds have been found to be competitive inhibitors including:

17β-N,N-diisopropylcarboxamide-3-nitro-5-α-androst-3-ene,

17β-N-t-butylcarboxamide-3-nitro-5-α-androst-3-ene, and

17β-N,N-diisopropylcarboxamide-3-nitro-5-α-androst-2-ene.

Compounds that are considered to be uncompetitive steroid 5-α-reductase inhibitors as described above include:

N-t-butyl-androst-3,5-diene-17β-carboxamide-3-carboxylic acid or a salt thereof, N,N-diisopropyl-androst-3,5-diene-17β-carboxamide-3-carboxylic acid or a salt thereof, 17β-(N,N-diisopropylcarboxamide)-estra-1,3,5(10)-triene-3-carboxylic acid or a salt thereof, 17β-(N-t-butylcarboxamide)-estra-1,3,5(10)-triene-3-carboxylic acid or a salt thereof, 17β-(N,N-diisopropylcarboxamide)-estra-1,3,5(10)-triene-3-sulfonic acid or a salt thereof, 20-α-(hydroxymethyl)-A-nor-5-α-pregn-1-ene-2-carboxylic acid or a salt thereof, 17β-(N-t-butylcarboxamide)-estra-1,3,5(10)-triene-3-sulfonic acid or a salt thereof, 17β-(N,N-diisopropylcarboxamide)-estra-1,3,5(10)-triene-3-phosphonic acid or a salt thereof, 17β-(N-t-butylcarboxmide)-estra-1,3,5(10)-triene-3-phosphonic acid or a salt thereof, 17β-(N,N-diisopropylcarboxamide)estra-1,3,5(10)-triene-3-phosphonic acid or a salt thereof, 17β-(N-t-butylcarboxamide)-estra-1,3,5(10)-triene-3-phosphonic acid or a salt thereof, 17β-N-t-butylcarboxamide-androst-3,5-diene-3-phosphinic acid or a salt thereof, 17β-N,N-diisopropylcarboxamide-androst-3,5-diene-3-phosphinic acid or a salt thereof, 17β-N-t-butylcarboxamide-androst-3,5-diene-3-phosphonic acid or a salt thereof, and 17β-N,N-diisopropylcarboxamide-androst-3,5-diene-3-phosphonic acid or a salt thereof.

Persons skilled in the art can readily determine if an inhibitor is a competitive or an uncompetitive type by the method set forth above. All such compounds are included within the scope of this invention.

Because the claimed combinations inhibit steroid 5-α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy, and male pattern baldness.

Certain combinations of the invention were tested for their in vivo potency in inhibiting steroid 5-α-reductase activity.

When male rats are castrated and allowed to go untreated for 1 month, the ventral prostates involutes to approximately 10% of its original total cell number. If exogeneous testosterone is given to these castrated rats to restore the physiological serum level of testosterone, the involuted ventral prostate rapidly proliferates restoring its original cell content within 2–3 weeks. Using the ability to inhibit this testosterone induced regrowth of the rat ventral prostate, the efficacy and potency of twice daily oral administering of the "competitive" inhibitor and the "uncompetitive" inhibitor individually and in combination were compared.

The competitive inhibitor being N-t-butyl-5-α-androst-1-ene-4-aza-17β-carboxamide -3-one (Compound A) and the uncompetitive inhibitor being N-t-butyl-androst -3,5-diene-17β-carboxamide-3-carboxylic acid (Compound C).

To perform these experiments, a total of 50 male Sprague Dawley rats (From Harlan Sprague-Dawley, Inc.) of 250–300 gm starting weight were used. Forty-five of these animals were castrated and allowed to go untreated for 1 month to produce maximal ventral prostatic and seminal vesicle involution. After this 1 month period, 40 of the 45 castrated animals were implanted subcutaneously in the flank with a 2.5 cm long testosterone filled silastic capsule. The 50 animals were set up in 10 groups as follows:

Group 1—intact rats fed twice a day with vehicle alone (intact controls).

Group 2—castrated rats fed twice a day with vehicle and not implanted with testosterone capsule (castrate controls).

Group 3—castrated rats implanted with a testosterone capsule fed twice a day with vehicle (restoration control).

Group 4—castrated rats plus testosterone implant plus uncompetitive inhibitor (BID) 12.5 mg/kg.

Group 5—castrated rats plus testosteroneimplant plus uncompetitive inhibitor (BID) 25 mg/kg.

Group 6—castrated rats plus testosterone implant plus uncompetitive inhibitor (BID) 50 mg/kg.

Group 7—castrated rats plus testosterone implant plus competitive inhibitor (BID) 12.5 mg/kg.

Group 8—castrated rats plus testosterone implant plus competitive inhibitor (BID ) 25 mg/kg.

Group 9—castrated rats plus testosterone implant plus competitive inhibitor (BID) 50 mg/kg.

Group 10—castrated rats plus testosterone implant plus uncompetitive inhibitor (BID) 50 mg/kg plus competitive inhibitor (BID) 50 mg/kg.

The animals were administered the 5-α-reductase inhibiting compounds twice a day (BID) for 10 consecutive days. This test compound was dissolved in propylene glycol and diluted in normal saline. At the end of the treatment period blood was collected from the animals and then they were sacrificed, the ventral prostrates were excised and weighed, and DHT levels were measured by the following procedure.

Prostate tissue was excised, trimmed, weighed, minced and washed with phosphate buffer. The tissue then was homogenized in phosphate buffer and extracted by addition of ethyl acetate and mixing on an orbital mixer for forty-five minutes. The ethyl acetate was evaporated, the residue was reconstituted in ethanol, and was centrifuge filtered using 0.45 gM filter paper. The components then were separated using reverse-phase HPLC collecting the DHT fraction. The fraction was reduced to dryness and reconstituted in standard commercial DHT assay buffer. DHT levels then were measured using standard techniques such as radioimmunoassay.

In the rats treated with increasing amounts of a single inhibitor the realized prostate weight reduction plateaued at significantly higher levels than in the castrated control model, while in the combination-treated rats the prostate weights were reduced to castrate levels. This plateau dose-response effect regarding the competitive inhibitor compound A has also been reported in other studies (Stoner, et al. (1987). *Endocrinology*, 120:774). Thus, the administration of the claimed combinations produces prostate weight reduction levels significantly lower than can be obtained by a single inhibitor alone.

The claimed combinations are incorporated into convenient dosage forms such as capsules, tablets, or injectable preparations. Solid or liquid pharmaceutical carders are employed. Solid carders include starch, lactose, calcium sulfate dihydrate, terra alba, sucrose, talc, gelatin, agar, pectin, acacia, magnesium stearate, and stearic acid. Liquid carders include syrup, peanut oil, olive oil, saline, and water. Similarly, the carder or diluent may include any prolonged release material, such as glyceryl monostearate or glyceryl distearate, alone or with a wax. The amount of solid carder varies widely but, preferably, will be from about 25 mg to about 1 g per dosage unit. When a liquid carder is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

The pharmacokinetic properties of each active component of the claimed invention must be contemplated when formulating conventional dosage regimens. To maximize its therapeutic effect, the individual compounds of the claimed combinations and compositions can be administered as a single pharmaceutical composition or consecutively in separate pharmaceutical compositions ("coadministered" as described herein). For example, one or more components can be incorporated into a timed release dosage unit form in which several doses are treated for delayed or sustained release of the medicament. Such dosage units may comprise sustained release granules, sugar centered spheres or multilayered tablets in each of which the availability of the active ingredient is controlled by coating with a lipid or polymeric material.

Doses of the present combinations in a pharmaceutical dosage unit as described above will be an efficacious, nontoxic quantity preferably selected from the range of 0.1–1000 mg/kg of each active compound, preferably 1–100 mg/kg. When treating a human patient in need of 5-α-reductase inhibition, the selected dose is administered preferably from 1–6 times daily, orally or parenterally. Preferred forms of parenteral administration include topically, rectally, transdermally, by injection and continuously by infusion. Oral dosage units for human administration preferably contain from 1 to 500 mg of active compound. Oral administration, which uses lower dosages is preferred. Parenteral administration, at higher dosages, however, also can be used when safe and convenient for the patient.

The method of this invention of inhibiting steroid 5-α-reductase activity in mammals, including humans, comprises administering internally to a subject in need of such inhibition an effective combination of steroid 5-α-reductase inhibiting compounds having both competitive and uncompetitive mechanisms of action.

Following are the results of testing the combinations of this invention:

Table 1

Effects of various treatments-with N-t-butyl-5-α-androst-1-ene-4-aza-17β-carboxamide-3-one (compound A) and N-t-butyl-androst-3,5-diene-17β-carboxamide-3-carboxylic acid (compound C) on the testosterone induced regrowth of the involuted ventral prostate and seminal vesicle of castrated male rats.

TABLE I

| Group No. | Treatment (N = 5 rats/group) | Ventral Prostate weight (mg/gland) | Ventral Prostate DNA (μg/gland) | Seminal Vesicle weight (mg/gland) | Seminal Vesicle DNA (μg/gland) |
|---|---|---|---|---|---|
| Group 1 | None (Intact control) | 639 ± 54 | 1443 ± 109 | 332 ± 38 | 1083 ± 63 |
| Group 2 | Castrated (castrate control) | 26 ± 3 | 165 ± 21 | 57 ± 3 | 508 ± 78 |
| Group 3 | Castrated + testosterone (restoration control) | 416 ± 32 | 817 ± 97 | 319 ± 19 | 1000 ± 121 |
| | Castrated + testosterone + compound C | | | | |
| Group 4 | BID - 12.5 mg/kg | 154 ± 22 | 359 ± 36 | 158 ± 15 | 851 ± 47 |
| Group 5 | BID - 25 mg/kg | 143 ± 17 | 383 ± 29 | 170 ± 19 | 890 ± 58 |
| Group 6 | BID - 50 mg/kg | 147 ± 15 | 316 ± 52 | 159 ± 20 | 855 ± 63 |
| | Castrated + testosterone + compound A | | | | |
| Group 7 | BID - 12.5 mg/kg | 71 ± 11 | 289 ± 17 | 118 ± 5 | 692 ± 51 |
| Group 8 | BID - 25 mg/kg | 55 ± 7 | 290 ± 25 | 108 ± 10 | 708 ± 72 |
| Group 9 | BID - 50 mg/kg | 62 ± 7 | 284 ± 19 | 108 ± 7 | 698 ± 39 |
| Group 10 | Castrated + testosterone + compound C (BID) 50 mg/kg + compound A (BID) 50 mg/kg | 33* ± 7 | 169* ± 13 | 88* ± 3 | 540* ± 42 |

*Statistically significant

The data in the above table demonstrates the synergistic effects of the "competitive" and "uncompetitive" steroid 5-α-reductase inhibitor combination on blocking testosterone induced regrowth of the involuted rat ventral prostate. Additionally, data was obtained showing that the testosterone levels were uneffected in all groups except in the castrate control.

No unacceptable toxicological effects are expected when compositions of the invention are administered in accordance with the present invention.

In addition, the 5-α-reductase inhibiting compounds disclosed in the present invention can be co-administered with further active ingredients, such as other compounds known to treat the disease states of acne vulgaris, seborrhea, female hirsutism, male pattern baldness, benign prostate hypertrophy or prostatic adenocarcinoma. Particularly preferred is the co-administeration of a 5-α-reductase inhibitor, as disclosed herein, or a composition containing a competitive inhibitor of 5-α-reductase and an uncompetitive inhibitor of 5-α-reductase, as disclosed herein, and minoxidil for use in the treatment of male pattern baldness (alopecia).

By the term "minoxidil" as used herein is meant the compound of the formula:

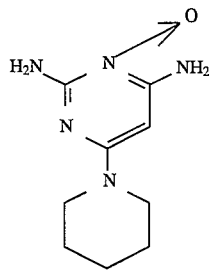

chemically minoxidil is designated as 2,4-pyrimidineadiamine, 6-(1-piperidinyl)-,3-oxide. Minoxidil is the active ingredient in Rogaine(®) which is sold as topical solution for stimulating hair growth by the Upjohn Company, Kalamazoo, Mich.

As used herein, when a composition containes a 5-α-reductase inhibitor, as described herein and a further active ingredient, said 5-α-reductase inhibitor can be co-administered with said further active ingredient.

By the term "co-administering" and derivatives thereof as used herein is meant either simultaneous administration or any manner of consecutive administration of a 5-α-reductase inhibiting compound, as described herein, and a further active ingredient or ingredients, such as other compounds known to treat the disease states of acne vulgaris, seborrhea, female hirsutism, male pattern baldness, benign prostate hypertrophy or prostatic adenocarcinoma. Preferably, if the administration is not simultaneous, the compounds are administered in a close time proximity to each other. Furthermore, it does not matter if the compounds are administered in the same dosage form, e.g. one active compound may be administered transdermally and another active compound may be administered orally.

The following examples illustrate preparation of the claimed combinations and pharmaceutical compositions containing these compounds. The examples are not intended to limit the scope of the invention as defined hereinabove and as claimed below.

EXAMPLE 1

An oral dosage form for administering the claimed compounds and compositions is produced by screening, mixing and filling into hard gelatin capsules the ingredients in the proportions shown in Table II below.

TABLE II

| Ingredients | Amounts |
| --- | --- |
| N-t-butyl-5-α-androst-1-ene-4-aza-17β-carboxamide-3-one | 100 mg |
| N-t-butyl-androst-3,5-diene-17β-carboxamide-3-carboxylic acid | 100 mg |
| Magnesium stearate | 20 mg |
| Lactose | 300 mg |

EXAMPLE 2

The sucrose, calcium sulfate dihydrate and claimed compounds and compositions shown in Table III below, are mixed and granulated in the proportions shown with a 10% gelatin solution. The wet granules are screened, dried, mixed with the starch, talc and stearic acid, screened and compressed into a tablet.

TABLE III

| Ingredients | Amounts |
| --- | --- |
| N-t-butyl-5-α-androst-1-ene-4-aza-17β-carboxamide-3-one | 100 mg |
| N-t-butyl-androst-3,5-diene-17β-carboxamide-3-carboxylic acid | 100 mg |
| Calcium sulfate dihydrate | 300 mg |
| Sucrose | 40 mg |
| Starch | 20 mg |
| Talc | 10 mg |
| Stearic acid | 6 mg |

EXAMPLE 3

N-t-butyl-5-α-androst-1-ene-4-aza-17β-carboxamide-3-one, 75 mg and N-t-butyl-androst -3,5-diene-17β-carboxamide-3-carboxylic acid, 75 mg, are dispersed in 25 ml of normal saline to prepare an injectable preparation.

EXAMPLE 4

The following compounds (expressed as base weight) are mixed together with 250 mg of lactose and 10 mg of magnesium stearate then filled into a hard gelatin capsule. These capsules are administered to a patient in need of steroid 5-α-reductase inhibiting activity from 1–6 times daily.

A. N-t-butyl-5-α-androst-1-ene-4-aza-17β-carboxamide-3-one, 100 mg; N-t-butyl-androst-3,5odiene-17β-carboxamide-3-carboxylic acid, 100 mg.

B. N-t-butyl-5-α-androst-1-ene-4-aza-17β-carboxamide-3-one, 100 mg; 17β-(N-t-butylcarboxamide)-ester-1,3,5(10)-triene-3-carboxylic acid, 100 mg.

C. 17β-N-t-butylcarboxamide-3-nitro-5-α-androst-3-ene, 100 mg; N-t-butyl -androst-3,5-diene-17β-carboxamide-3-carboxylic acid, 100 mg.

D. 17β-N-t-butylcarboxamide-3-nitro-5-α-androst-3-ene, 100 mg; 17β-(N-t-butylcarboxamide) -ester-1,3,5(10)-triene-3-carboxylic acid, 100 mg.

While the preferred embodiments of the invention are illustrated by the above, it is to be understood that the invention is not limited to the precise instructions herein disclosed and that the fight to all modifications coming within the scope of the following claims is reserved.

What is claimed is:

1. A composition comprising an uncompetitive inhibitor of steroid 5-α-reductase and a compound selected from the group consisting of:

N-t-butyl-5-α-androst-1ene-4-aza-17β-carboxamide-3-one;

17β-N,N-diisopropylcarboxamide-3-nitro-5-α-androst-3ene;

17β-N-t-butylcarboxamide-3-nitro-5-α-androst-3-ene; and

17β-N,N-diisopropylcarboxamide-3-nitro-5-α-androst-2-ene.

2. A composition comprising a competitive inhibitor of steroid 5-α-reductase and a compound selected from the group consisting of:

N-t-butyl-androst-3,5-diene-17β-carboxamide-3-carboxylic acid or a salt thereof;

N,N-diisopropyl-androst-3,5-diene-17β-carboxamide-3-carboxylic acid or a salt thereof;

17β-(N,N-diisopropylcarboxamide)-estra-1,3,5(10)-triene-3-carboxylic acid or a salt thereof;

17β-t-butylcarboxamide)-estra-1,3,5(10)-triene-3-carboxylic acid or a salt thereof;

17β-(N,N-diisopropylcarboxamide)-estra-1,3,5(10)-triene-3-sulfonic acid or a salt thereof;

17β-(N-t-butylcarboxamide)-estra-1,3,5(10)-triene-3-sulfonic acid or a salt thereof;

17β(N,N-diisopropylcarboxamide)-estra-1,3,5(10)-triene-3-phosphonic acid or a salt thereof;

17β-(N-t-butylcarboxmide)-estra-1,3,5(10)-triene-3-phosphonic acid or a salt thereof;

17β-(N,N-diisopropylcarboxamide)estra-1,3,5(10)-triene-3-phosphonic acid or a salt thereof;

20-α-(hydroxymethyl)-A-nor-5-α-pregn-1-ene-2-carboxylic acid or a salt thereof;

17β-(N-t-butylcarboxamide)-estra-1,3,5(10)-triene-3-phosphonic acid or a salt thereof;

17β-N-t-butylcarboxamide-androst-3,5-diene-3-phosphinic acid or a salt thereof;

17β-N,N-diisopropylcarboxamide-androst-3,5-diene-3-phosphinic acid or a salt thereof;

17β-N-t-butylcarboxamide-androst-3,5-diene-3-phosphonic acid or a salt thereof; and 17β-N,N-diisopropylcarboxamide-androst-3,5-diene-3-phosphonic acid or a salt thereof.

3. The composition of claim 1 in which the uncompetitive inhibitor is N-t-butyl-androst -3,5-diene-17β-carboxamide-3-carboyxlic acid or a salt thereof.

4. The composition of claim 2 in which the competitive inhibitor is N-t-butyl-5-α-androst -1-ene-4-aza-17β-carboxamide-3-one.

5. A pharmaceutical composition comprising a composition of claim 1 and a pharmaceutically acceptable carrier.

6. A pharmaceutical composition comprising a composition of claim 2 and a pharmaceutically acceptable carrier.

7. A method of inhibiting steroid 5-α-reductase activity in mammals, which comprises the administration to mammals in need of such treatment, an effective amount of a composition of claim 1.

8. A method of inhibiting steroid 5-α-reductase activity in mammals, which comprises the administration to mammals in need of such treatment, an effective amount of a composition of claim 2.

9. A method of reducing or maintaining prostate size in mammals, which comprises the administration to mammals in need of such treatment, an effective amount of a composition of claim 1.

10. A method of reducing or maintaining prostate size in mammals, which comprises the administration to mammals in need of such treatment, an effective amount of a composition of claim 2.

11. The method of inhibiting steroid 5-α-reductase activity in mammals in need thereof which comprises administering to the subject consecutively, in separate pharmaceutical compositions, an uncompetitive inhibitor of steroid 5-α-reductase and a compound selected from the group consisting of:

N-t-butyl-5-α-androst-1-ene-4-aza-17β-carboxamide-3-one;

17β-N,N-diisopropylcarboxamide-3-nitro-5-α-androst-3ene;

17β-N-t-butylcarboxamide-3-nitro-5-α-androst-3-ene; and

17β-N,N-diisopropylcarboxamide-3-nitro-5-α-androst-2-ene.

12. The method of inhibiting steroid 5-α-reductase activity in mammals in need thereof which comprises administering to the subject consecutively, in separate pharmaceutical compositions, a competitive inhibitor of steroid 5-α-reductase and a compound selected from the group consisting of:

N-t-butyl-androst-3,5-diene-17β-carboxamide-3-carboxylic acid or a salt thereof;

N,N-diisopropyl-androst-3,5-diene-17β-carboxamide-3-carboxylic acid or a salt thereof;

17β-(N,N-diisopropylcarboxamide)-estra-1,3,5(10)-triene-3-carboxylic acid or a salt thereof;

17β-(N-t-butylcarboxamide)-estra-1,3,5(10)-triene-3-carboxylic acid or a salt thereof;

17β-(N,N-diisopropylcarboxamide)-estra-1,3,5(10)-triene-3-sulfonic acid or a salt thereof;

17β-(N-t-butylcarboxamide)-estra-1,3,5(10)-triene-3-sulfonic acid or a salt thereof;

17β-(N,N-diisopropylcarboxamide)-estra-1,3,5(10)-triene-3-phosphonic acid or a salt thereof;

17β-(N-t-butylcarboxmide)-estra-1,3,5(10)-triene-3-phosphonic acid or a salt thereof;

17β-(N,N-diisopropylcarboxamide)estra-1,3,5(10)-triene-3-phosphonic acid or a salt thereof;

20-α-(hydroxymethyl)-A-nor-5-α-pregn-1-ene-2-carboxylic acid or a salt thereof;

17β-(N-t-butylcarboxamide)-estra-1,3,5(10)-triene-3-phosphonic acid or a salt thereof;

17β-N-t-butylcarboxamide-androst-3,5-diene-3-phosphinic acid or a salt thereof;

17β-N,N-diisopropylcarboxamide-androst-3,5-diene-3-phosphinic acid or a salt thereof;

17β-N-t-butylcarboxamide-androst-3,5-diene-3-phosphonic acid or a salt thereof; and 17β-N,N-diisopropylcarboxamide-androst-3,5-diene-3-phosphonic acid or a salt thereof.

* * * * *